(12) United States Patent
Nissing

(10) Patent No.: US 6,270,875 B1
(45) Date of Patent: *Aug. 7, 2001

(54) MULTIPLE LAYER WIPE

(75) Inventor: Nicholas James Nissing, Cincinnati, OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/231,476

(22) Filed: Jan. 14, 1999

Related U.S. Application Data

(60) Provisional application No. 60/072,475, filed on Jan. 26, 1998.

(51) Int. Cl.[7] ............................................. B23B 7/00
(52) U.S. Cl. ..................... 428/138; 428/153; 428/154; 428/156
(58) Field of Search ...................... 428/153, 154, 428/156, 138

(56) References Cited

U.S. PATENT DOCUMENTS

| | | | |
|---|---|---|---|
| 3,301,746 | 1/1967 | Sanford et al. | 162/113 |
| 3,375,156 | 3/1968 | Edgar, Jr. | 162/132 |
| 3,536,563 * | 10/1970 | Brandts et al. | 156/246 |
| 3,546,056 | 12/1970 | Thomas | 161/57 |
| 3,597,299 | 8/1971 | Thomas et al. | 161/57 |
| 3,615,976 | 10/1971 | Endres et al. | 156/83 |
| 3,650,882 | 3/1972 | Thomas | 161/122 |
| 3,684,641 | 8/1972 | Murphy | 161/129 |
| 3,695,985 | 10/1972 | Brock et al. | 161/129 |
| 3,708,383 | 1/1973 | Thomas et al. | 161/57 |
| 3,709,750 | 1/1973 | Minshell | 156/72 |
| 3,755,062 | 8/1973 | Schirmer | 161/146 |
| 3,881,210 | 5/1975 | Drach et al. | |
| 3,925,127 | 12/1975 | Yoshioka | 156/85 |
| 3,929,135 | 12/1975 | Thompson | 128/287 |
| 3,953,638 | 4/1976 | Kemp | 428/154 |
| 3,994,771 | 11/1976 | Morgan et al. | 162/113 |
| 4,300,981 | 11/1981 | Carstens | 162/109 |
| 4,324,246 | 4/1982 | Mullane et al. | 128/287 |
| 4,342,314 | 8/1982 | Radel et al. | 128/287 |
| 4,440,597 | 4/1984 | Wells et al. | 162/111 |
| 4,463,045 | 7/1984 | Ahr et al. | 428/131 |
| 4,469,735 | 9/1984 | Trokhan | 428/154 |
| 4,522,863 | 6/1985 | Keck et al. | 428/196 |
| 4,525,407 | 6/1985 | Ness | 428/138 |
| 4,529,480 | 7/1985 | Trokhan | 162/109 |
| 4,637,819 | 1/1987 | Ouellette et al. | 604/369 |
| 4,637,859 | 1/1987 | Trokhan | 162/109 |
| 4,661,389 | 4/1987 | Mudge et al. | 428/110 |
| 4,695,422 | 9/1987 | Curro et al. | 264/504 |
| 4,778,644 | 10/1988 | Curro et al. | 264/557 |
| 4,839,216 | 6/1989 | Curro et al. | 428/134 |
| 4,842,596 * | 6/1989 | Kielpikowski et al. | 604/385.2 |
| 4,847,134 | 7/1989 | Fahrenkrug et al. | 428/138 |
| 4,891,258 | 1/1990 | Fahrenkrug | 428/138 |

(List continued on next page.)

Primary Examiner—Elizabeth M. Cole
(74) Attorney, Agent, or Firm—Joan B. Tucker; Roddy M. Bullock

(57) ABSTRACT

A disposable wiping article is disclosed having at least a first layer and a second plastic film layer. The first layer has a wet extensibility greater than that of the second, layer. The first layer can be a dry creped web of cellulosic fibers, and the second layer can be an apertured, three dimensional plastic film. Selected portions of the first layer are bonded to the second layer to inhibit wet extension of the first layer in the plane of the first layer. In one embodiment, the wiping article comprises a third layer which can be a dry creped, apertured web of cellulosic fibers having a wet extensibility greater than that of the second layer. The second plastic film layer is disposed between the first layer and the third layer and inhibits wet extension of both the first and third layer when wetted.

18 Claims, 5 Drawing Sheets

U.S. PATENT DOCUMENTS

| | | | |
|---|---|---|---|
| 4,919,756 | 4/1990 | Sawdai | 162/111 |
| 5,006,394 | 4/1991 | Baird | 428/138 |
| 5,073,235 | 12/1991 | Trokhan | 162/199 |
| 5,223,096 | 6/1993 | Phan et al. | 162/158 |
| 5,227,228 | 7/1993 | Newell | 428/224 |
| 5,245,025 | 9/1993 | Trokhan et al. | 536/56 |
| 5,277,761 | 1/1994 | Phan et al. | 162/109 |
| 5,364,504 | 11/1994 | Smurkoski et al. | 162/116 |
| 5,401,557 | 3/1995 | Inomata et al. | 428/110 |
| 5,503,715 | 4/1996 | Trokhan et al. | 162/296 |
| 5,506,030 | 4/1996 | Landers et al. | 428/143 |
| 5,529,664 | 6/1996 | Trokhan et al. | 162/109 |
| 5,618,610 | 4/1997 | Tomita et al. | 428/152 |
| 5,623,888 | 4/1997 | Zafiroglu | 112/414 |
| 5,635,875 | 6/1997 | Biagioli et al. | 428/132 |
| 5,654,076 | 8/1997 | Trokhan et al. | 428/131 |

* cited by examiner

MULTIPLE LAYER WIPE

This application claim benefit to Provisional Application 60/072,475 filed Jan. 26, 1998.

FIELD OF THE INVETION

The present invention is related to disposable wiping articles, and more particularly to disposable wiping articles having two or more layers.

BACKGROUND OF TIE INVENTION

Disposable wiping articles are well known in the art. Such wiping articles typically have a substrate which includes one or more materials or layers. The substrate can be pre-moistened with a wetting agent prior to use, or alternatively, can be combined with a liquid at the point of use of the article. Pre-moistened wiping articles are also referred to as "wet wipes" and "towelettes."

Desirable features of such wiping articles include texture, caliper (thickness) and bulk (volume per unit weight). A relatively high value of texture is desirable for aiding in cleaning of surfaces. Wipe structures that result in increased texture upon wetting are particularly beneficial. Such structures may be achieved by utilizing multiple layers having differential wet extensibility. One such structure is disclosed in U.S. Pat. No. 4,469,735 issued Sep. 4, 1984 to Trokhan. However, increased texture does. not necessarily produce increased caliper. Relatively high values of caliper and bulk are desirable for providing volume in the article for receiving and containing liquids.

In addition to physical features such as texture, caliper, and bulk, other desirable properties of a wiping article include its propensity to create foam, its ability to maintain directional fluid flow, and its strength. For example, when used as a facial wipe, certain lotions or cleansers may be used with the wipe, and it would be desirable to generate a lather with the wipe. When used with a hard surface cleaner, for example on kitchen countertops, it would be desirable for the wipe to help produce sudsing of the detergent or surfactant. For entrapment of dirt, grime, and the like, it would be helpful if the wipe had the built-in ability to capture dirt, much like a filter. For all wiping tasks, particularly wet wiping, improved wet strength is beneficial. Wet strength is especially important for scrubbing applications.

Accordingly, it would be desirable to provide a disposable wiping article that exhibits increased texture and bulk upon wetting.

Additionally, it would be desirable to provide a disposable wiping article having a propensity to aid in generation of foam, suds, or lather in applications involving cleansers, detergents, lotions, and the like.

Additionally, it would be desirable to provide a disposable wiping article having a propensity to aid in entrapment of dirt, grime, and the like, upon wiping.

Further, it would be desirable to provide a disposable wiping article which has improved wet strength in wet wiping applications.

SUMMARY OF THE INVETION

The present invention provides a multiple layer disposable wiping article. The wiping article includes at least at least two layers, or plies. The first layer is extensible in a plane of the first layer when wetted. The second layer comprises a plastic film which is less extensible when wetted than the first layer. Selected portions of the first layer are joined to the second layer to inhibit wet extension of the first layer in the plane of the first layer.

When the first layer is wetted, the second layer constrains extension of the first layer in the plane of the first layer. As a result, the first layer deforms, such as by buckling or puckering, in the Z-direction (perpendicular to the plane of the first layer).

The first layer can comprise a wetting agent prior to use of the article, which provides wetting of the first layer. The wetting agent can be an aqueous lotion. Preferably, selected portions of the first layer are joined to the second layer in a predetermined bonding pattern to provide a plurality of unbonded regions of the first layer.

The second layer preferably comprises a three dimensional formed film having a caliper of about 20 mils (0.020 inch). The three dimensional film can provide caliper, bulk, and texture independent of the caliper, bulk, and texture provided by puckering of the first layer. The plastic film can be a macroscopically expanded three dimensional plastic film.

In one embodiment, the disposable wiping article comprises three layers: a first cellulosic layer, a second layer comprising a three dimensional apertured plastic film and an apertured third layer. The third layer can comprise a dry creped, aperturedt web of cellulosic fibers. The second layer is disposed intermediate the first layer and the third layer. The apertures in the third layer can be larger than the apertures in this second layer to provide two stage filtering of small particles.

BRIIEF DESCRIPTION OF THfE DRAWINGS

DETAILED DESCRIPTION OF THE INVENTION

FIGS. 1 and 3A–3D illustrate a two-layer, or two-ply, embodiment of the present invention. FIGS. 2 and 4 illustrate a three-layer embodiment of the present invention.

Referring to FIGS. 1 and 3A–3D, the present invention comprises a multiple layer disposable wiping article 100. The disposable wiping article 100 comprises a first layer 1000 and a second layer 2000.

The first layer 1000 is extensible, and in particular is extensible when wetted, i.e., the first layer is wet extensible. By "wet extensible" it is meant the tendency to elongate in at least one direction when wetted. In general, "wetted" refers to wetting with aqueous solutions, including water, capable of inducing extension in the extensible first layer. For example, water relaxes the crepe in foreshortened paper, thereby causing an extension of the paper in at least one direction in the plane of the paper. While not wishing to bound by theory, the relaxation of crepe may be a result of the loss of hydrogen bonds within the paper structure due to the presence of water. However, any fluid, mixture, or solution which could cause this crepe relaxation would be considered to "wet" the article. The second layer 2000 is relatively less extensible than the first layer 1000, including when wetted. Extensibility is measured according to the "Wet Extensibility Test" described below, and is reported as a percentage.

As more fiflly described below, first layer 1000 is foreshortened, and is preferably a creped paper layer. Foreshortening can be accomplished by creping the paper from a rigid surface, and preferably from a cylinder. A Yankee drying drum is commonly used for this purpose. Creping is accomplished with a doctor blade as is well known in the art. Creping may be accomplished according to commonly assigned U.S. Pat. No. 4,919,756, issued Apr. 24, 1990 to Sawdai, the disclosure of which is incorporated herein by reference. Alternatively or additionally, foreshortening may be accomplished via wet microcontraction as taught in commoinly assigned U.S. Pat. No. 4,440,597, issued Apr. 3, 1984 to Wells et al., the disclosure of which is incorporated herein by reference.

Figure 1:
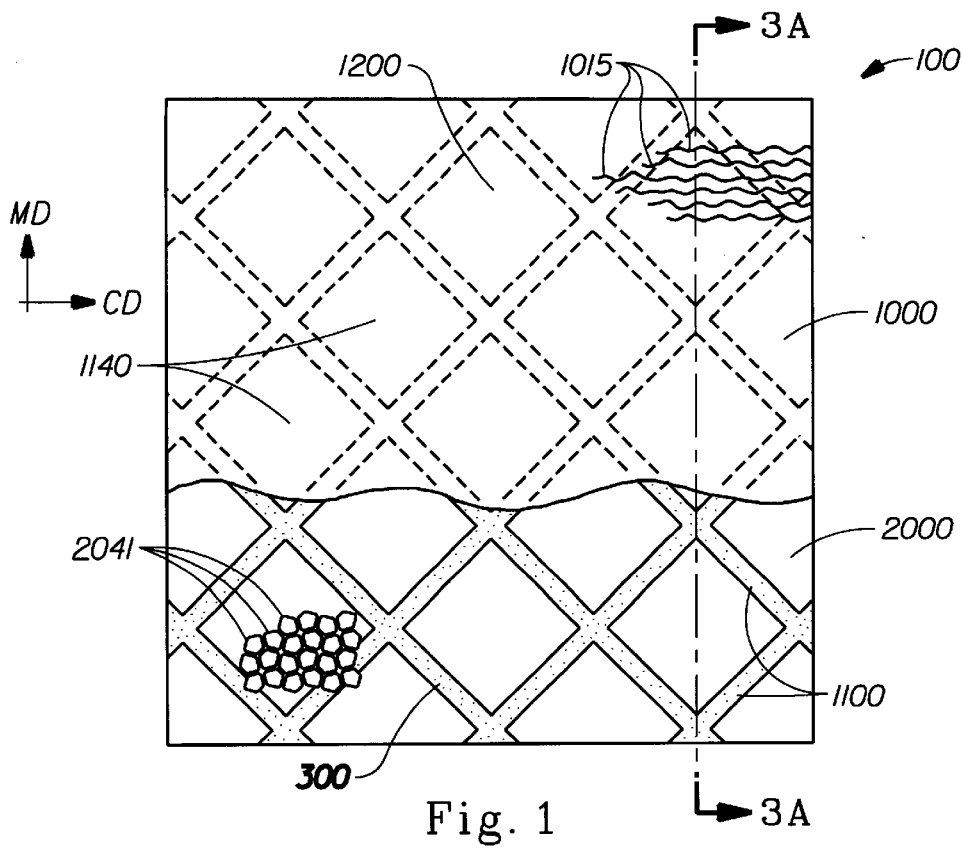
FIG. 1 is a plan view of a two-layer embodiment of the present invention, showing a dry creped first layer joined to a formed filmn second layer.
Figure 2:
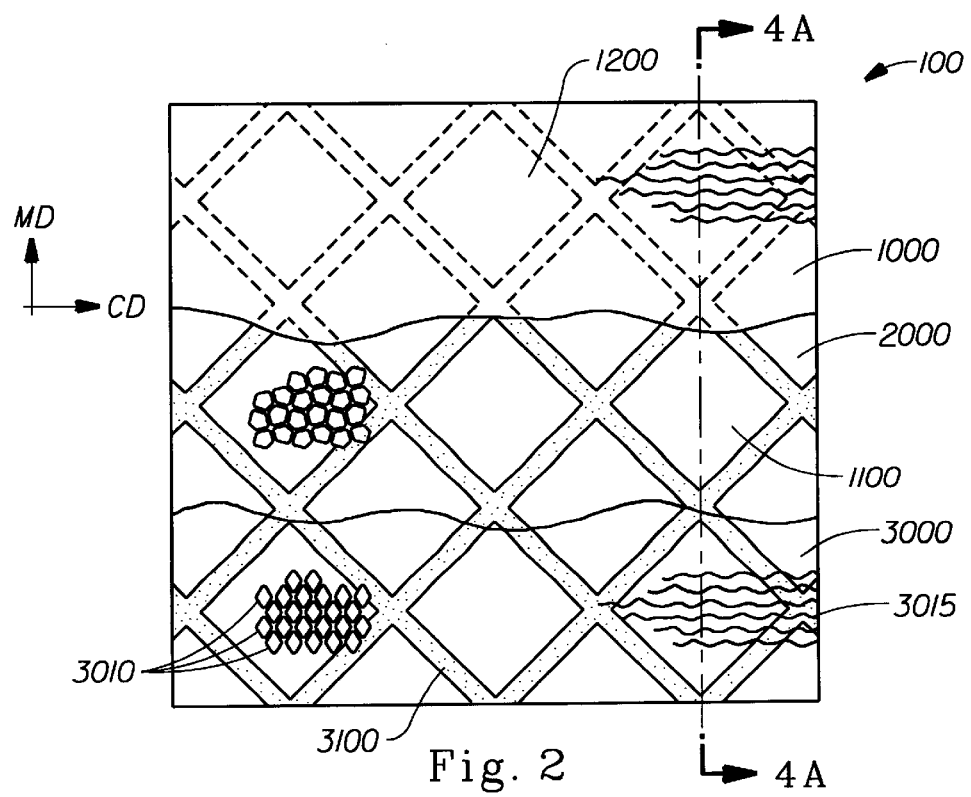
FIG. 2 is a plan view of a three-layer embodiment of the present invention, showing a dry creped first layer joined to one side of a formed film second layer, and an apertured third layer joined to the other side of the formed film second layer.

As shown in FIG. 1, crepe ridges 1015 are formed during paper manufacture, generally perpendicular to the machine direction, MD, as indicated in FIG. 1. Creping can provide the foreshortening of the first layer which allows wet extensibility in the first layer. Second layer 2000 is preferably a polymer film, for example, a thermoplastic film, which is substantially less wet extensible than first layer 1000. In a preferred embodiment, second layer 2000 is an apertured, formed film, as more fully described below in the section entitled "Second Layer" with reference to FIG. 5. Openings, or apertures in second layer 2000 form capillaries 2041, fluid communication and directional fluid flow, as well as provide for improved texture for increased effectiveness in cleaning applications.

Selected portions of the first layer 1000 are joined, directly or indirectly, to second layer 2000 to inhibit wet extension of the first layer in the plane of the first layer. In FIGS. 1 and 3A–3D, selected portions of the first layer 1000 are joined to the second layer 2000 to provide continuous bonded regions designated 1100, defining discrete unbonded regions 1140. In a preferred embodiment shown in FIG. 1, the bonded regions 1100 are shown as a continuous network of intersecting lines forming generally diamond-shaped unbonded regions 1140. The width and spacing of the intersecting lines of bonded regions 1100 may be adjusted to provide a desired pattern, that is, a desired size and spacing of diamond-shaped unbonded regions 1140.

An adhesive, for example, a hot melt adhesive, designated by reference numeral 300 in FIG. 1, can be used to join the first layer 1000 to second layer 2000. One suitable adhesive is an ethylene vinyl acetate (hereinafter EVA) hot melt adhesive commercially available as H1382-01 from Ato-Findley Adhesives of Wauwatosa, Wis.

As used herein, "continuous network" refers to a macroscopic pattern of the bonded region 1100, ie., the bond pattern appears to be continuous, defining distinct, discrete unbonded regions. The pattern may also be essentially continuous, meaning that the network may be comprised of closely spaced, discrete bond sites, that as a whole form a continuous pattern defining discrete unbonded regions. The continuous network of intersecting lines may be virtually any pattern, resulting in unbonded regions of virtually limitless geometric shapes, including, for example, squares, rectangles, and triangles. As well, the network need not be completely continuous, nor limited to a pattern of straight or uniform lines, but may, for example, be a network resulting in circular, oval, or other non-polygonal geometrically-shaped unbonded regions.

Alternatively, while a continuous network is currently preferred, it is contemplated that dis-continuous, or essentially continuous, bond patterns may also provide for the desired caliper increase according to present invention. For example, bonded areas comprising open circles or other closed figures can be sufficient to permit unbonded regions to increase in caliper. It is contemplated that having discontinuous bond sites, such as a pattern of spot bonds, can also provide for sufficient constraint so as to force first layer 1000 into out of plane deformation upon wetting. Without wishing to be bound by theory, in principle, the more a particular bond pattern approaches a continuous network bounding discrete unbonded regions, the more pronounced are the benefits of the present invention.

Because of the relatively lower wet extensibility of the second layer 2000, and due to the bonding of first layer 1000 to second layer 2000, the second layer 2000 constrains extension of the first layer 1000 in the plane of the first layer. As a results when wetted, the first layer 1000 deforms, such as by buckling or puckering, in thme Z-direction (perpendicular to the plane of the first layer, corresponding to the vertical direction in cross-sections shown in FIGS. 3A–D). The Z-direction is indicated in FIGS. 3A–D.

Figure 3A:
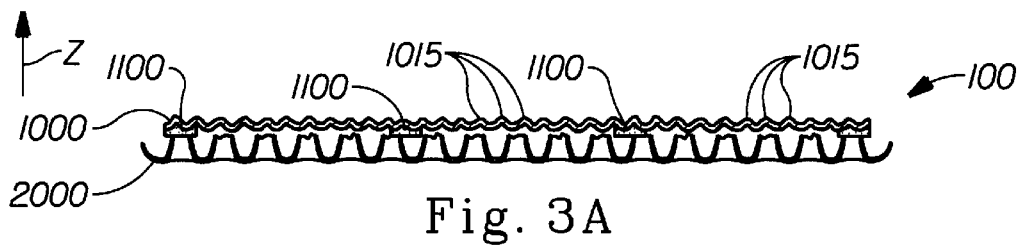
FIG. 3A is a cross-sectional illustration of a two layer embodiment of the present invention along Section 3—3 of FIG. 1, FIG. 3A showing the two-layer embodiment prior to wetting, and wherein the second layer is joined to the first lae to provide preferential flow through apertures in the second layer toward the first layer.
Figure 3B:
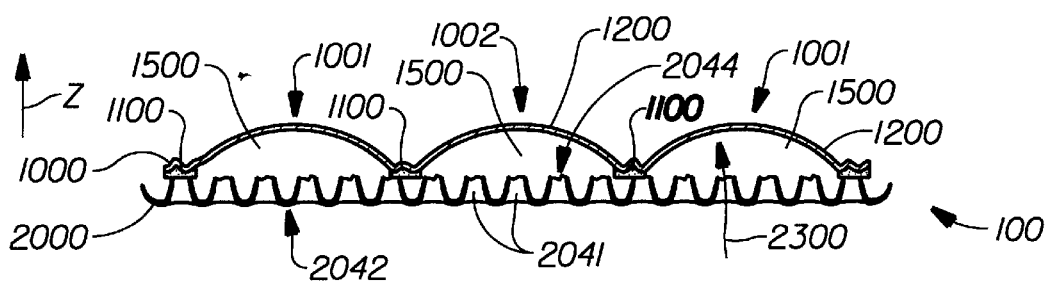
FIG. 3B is a cross-sectional illustration of a two layer embodiment of the present invention along Section 3—3 of FIG. 1 after the first layer has been wetted to provide deformation of the first layer perpendicular to the plane of the first layer.

FIGS. 3A–D show a portion of a wipe 100, for example the portion in Section 3—3 of FIG. 1. Referring to FIG. 3A, prior to wetting, first layer 1000 is bonded to second layer 2000 at regions 1100 in a relatively flat, smooth, configuration. First layer 1000 is foreshortened, e.g., creped, resulting in creping ridges 1015, generally in the plane of first layer 1000. Upon wetting, as shown in FIG. 3B, out-of-plane, Z-direction deformation of the first layer 1000 results from wet expansion of first layer 1000. The Z-direction is indicated in FIGS. 3A–D. First layer 1000 is shown in FIG. 3B after wet extension, with the crepe completely relaxed, but it is understood that complete relaxation of the crepe is not required to realize the benefits of the present invention.

Upon wetting of the first layer 1000, out-of-plane deformation provides the wipe 100 with elevated ridges 1001 (FIG. 3B) which increase the wet texture, wet caliper (thickness) and wet bulk of the wipe 100. Therefore, one beneficial property of a two layer wipe of the present invention is that the wet caliper is greater than the dry caliper. In particular, the wipe 100 can have a wet caliper to dry caliper ratio which is greater than 1.0, and is preferably at least about 1.1, more preferably at least about 1.2, and most preferably at least about 1.4. The wet caliper to dry caliper ratio is a measure of the thickness of the wipe 100, when wetted, relative to the thickness of the dry wipe 100 prior to wetting. The wet caliper to dty caliper ratio is measured according to the procedure "Wet Caliper to Dry Caliper Ratio" provided below.

The elevated ridges 1001 also provide pockets 1500 disposed between the unbonded portions of the first layer 1000 and the underlying portions of the second layer 2000. Without wishing to be bound by theory, it is believed that pockets 1500 can serve as containment areas for either wetting agents after wet extension, or for dirt and grime after cleaning. When configured as shown in FIGS. 3A and 3B, second layer 2000 is positioned so that capillary flow is directed into pockets 1500, thereby enabling filtering, or entrapment of particulates and other substances removed when the wipe is used in cleaning applications.

Second layer 2000 preferably has a more textured second surface on one side than the other, as more fully described below in the section entitled "Second Layer" with reference to FIG. 5. Having surfaces of different textures allows flexibility in designing preferred properties, for example, lathering capability, into a wipe of the present invention. In FIGS. 3A and 3B, the first layer 1000 is joined to the secoind layer 2000 such that the more textured second surface 2044 (see FIG. 5) faces toward the first layer 1000.

Texture differences between the two sides of second layer 2000 may be a result of the capillary structure of an apertured, three-dimensional formed film. The capillaries of a preferred formed film of the present invention also serve to provide for directional fluid flow of fluids in contact with wipe 100. The direction of flow is indicated by arrow 2300 in FIGS. 3B and 3C. The arrangement as shown in FIGS. 3A and 3B has the advantage that liquids and small particles can pass through the second layer 2000 and the small particles can be trapped in pockets 1500 between the first layer 1000 and the second layer 2000.

Figure 3C:
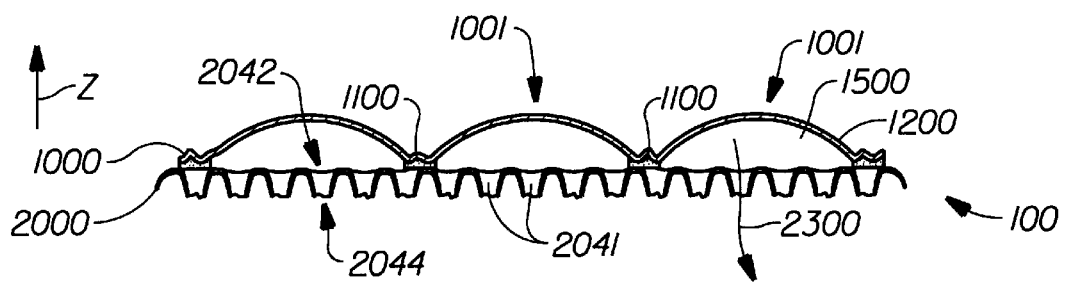
FIG. 3C is a cross-sectional illustration of an alternative two-layer embodiment of the present invention after wetting wherein the second layer is joined to the first layer to provide a relatively textured surface of the second layer facing outwardly.

In FIG. 3C, the first layer 1000 is joined to the second layer 2000 such that the first surface 2042 (see FIG. 5) faces toward the first layer 1000, and the more textured surface 2044 faces outwardly, away from the first layer 1000. Such an arrangement has the advantage that the textured surface 2044 can be utilized for more effective scrubbing in certain wet wiping applications, such as hard surface cleaning. In FIG. 3C, the second layer is oriented relative to the first layer such that the preferred direction of flow through the apertures in the second layer 2000 is away from the first layer 1000.

Figure 3D:
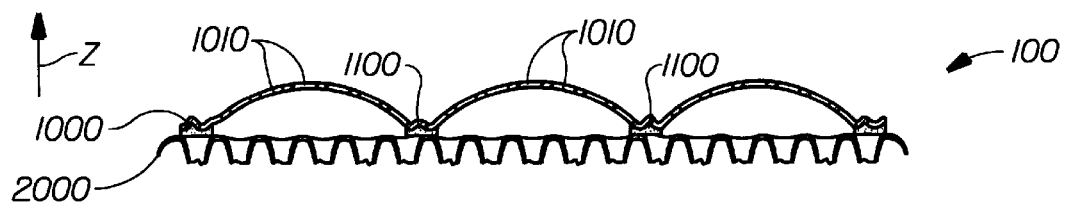
FIG. 3D is a cross-sectional illustration of an alternative two-layer embodiment of the present invention after wetting wherein the second layer is joined to the first layer that has been apertured.

FIG. 3D shows an alternative design, wherein first layer 1000 may be apertured. Apertures in first layer 1000, while not necessary to practice the present invention, add greatly to the desired texture and bulk of wipe 100. When all apertured first layer is used, the deformation of the wetted first layer 1000 again provides the wipe 100 with elevated ridges 1001 which increase the wet texture, wet caliper (thickness) and wet bulk of the wipe 100. However, in this alternative embodiment, the elevated ridges 1001 have apertures 1010 which provide a flow path through which liquids and/or small particles can enter the pockets 1500.

The first layer can comprise a wetting agent prior to use of the article, which provides wet extension of the first layer. The wetting agent can be an aqueous lotion (at least 50 percent by weight water).

FIRST LAYER:

Referring to the components of the article 100 in more detail, suitable materials from which the first layer 1000 can be formed include woven materials, nonwoven materials, foams, battings, and the like. The first layer 1000 can be constructed to have an extensibility of at least 4 percent, and more preferably has an extensibility of at least about 10 percent, even more preferably about 20 percent, and can be at least about 25 percent when wetted. Particularly preferred materials are nonwoven webs having fibers or filaments distributed randomly as in "air-laying" or certain "wet-laying" processes, or with a degree of orientation, as in certain "wet-laying" and "carding" processes.

The fibers or filaments of the first layer 1000 can be natural (e.g. cellulosic fibers such as wood pulp fibers, cotton linters, and bagasse fibers) or synthetic (e.g. polyolefins, polyamides or polyesters).

In one preferred embodiment, the first layer 1000 comprises a wetlaid web of cellulosic wood pulp fibers which has been foreshortened at least about 4 percent, and more preferably at least about 10 percent, even more preferably about 20 percent, and most preferably at least about 25 percent, such as by dry creping. Referring to FIGS. 1 and 3A, the first layer 1000 comprises crepe ridges 1015 corresponding to the foreshortening of the first layer 1000. In FIG. 3B the crepe ridges 1015 are not shown to indicate that the dry creping has been drawn out upon wetting and extension of the first layer 1000.

The first layer 1000 can have a basis weight of between about 15 and about 65 grams per square meter (gsm), and a caliper between about 4 mils (0.004 inch) and about 40 mils (0.040 inch). The first layer can comprise a paper web made according to the methods described in one or more of the following patents which are incorporated herein by reference: U.S. Pat. No. 3,301,746 (Sanford); U.S. Pat. No. 3,994,771 (Morgan) U.S. Pat. No. 4,300,981 (Carstens); U.S. Pat. No. 4,529,480 (Trokhan); U.S. Pat. No. 5,073,235 (Trokhan); U.S. Pat. No. 5,503,715 (Trokhan); U.S. Pat. No. 4,637,859 (Trokhan); U.S. Pat. No. 5,364,504 (Smurkoski et al.); and U.S. Pat. No. 5,529,664 (Trokhan et al.).

In one embodiment, the first layer 1000 comprises a paper web having multiple regions distinguished from one another by basis weight. The web can have a continuous high basis weight network, and discrete regions of low basis weight which circumscribe discrete regions of intermediate basis weight. Such a paper web is disclosed in U.S. Pat. No. 5,245,025 issued to Trokhan et al. on Sep. 14, 1993, which patent is incorporated herein by reference.

While not wishing to be bound by theory, it is believed that the paper strength can significantly alter the overall appearance of the complete article. The amount of foreshortening, such as by creping, of the first layer is proportional to the amount of planar expansion and thereby the amount of caliper generated upon wetting. However, if the wet strength of the paper article is insufficient, the "buckles" may collapse to form a more "wrinkled" product having less caliper. Therefore both crepe and wet strength can be adjusted to provide an amount of texture based on the intended use of the article. Wet burst measurements were measured by a Thwing-Albert Burst Tester model number 1300-77, which tested peak load of a fully wetted substrate. The test utilized a 0.5 in ball diameter, a 5 in/min ball velocity, and clamps the test sample around a 3.5 in. diameter circle perpendicular to the motion of the ball. Peak load wet burst strengths are between 100 and 1200 grams per ply. Morec preferably between 400 and 700 grams per ply and most preferably between 500 and 600 grams per ply.

SECOND LAYER:

The second layer 2000 constrains extension of the first layer 1000. The second layer 2000 comprises a plastic film having a wet extensibility less than that of the first layer 1000. The plastic film is preferably apertured, and can be formed from a polymeric film material such as polyethylene, polypropylene, or the like. It is desirable that the second layer comprise an apertured film because the apertures permit passage of air and liquid from one side of the article 100 to the other, thereby promoting the formation of foam when the article 100 comprises, or is used with, a liquid detergent.

Figure 5:
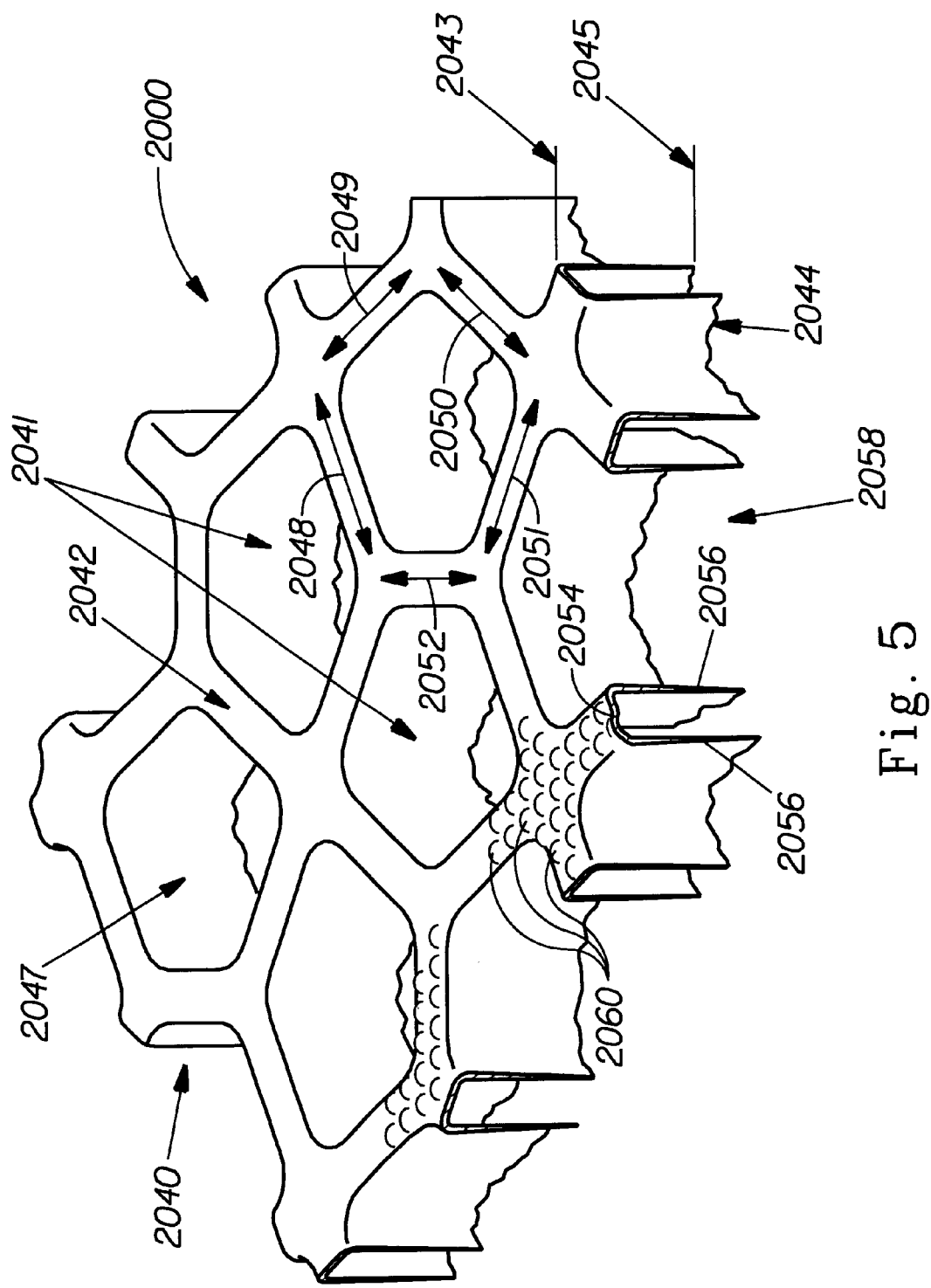
FIG. 5 is an enlarged, partially segmented perspective illustration of a three-dimensional, macroscopically-expanded formed film web suitable for use as the second layer in the present invention.

Preferably, the second layer 2000 comprises a three dimensional, macroscopically expanded formed film, as shown greatly enlarged in FIG. 5. An apertured formed film is preferred because the apertures in such a film can exhibit preferential fluid flow in one direction.

Preferably, second layer 2000 has a thickness of at least about 5 mils, more preferably at least about 10 mils, most preferably at least about 15 mils, to provide bulk and thickness independent of wetting of the article 100. In one embodiment, the second layer has a thickness of about 20 mils (0.020 inch).

Suitable formed films are disclosed in the following U.S. Patents, which are incorporated herein by reference: U.S. Pat. No. 3,929,135 (Thompson); U.S. Pat. No. 4,324,246 (Mullane); U.S. Pat. No. 4,342,314 (Radel); U.S. Pat. No. 4,463,045 (Ahr); U.S. Pat. No. 4,637,819 (Oullette); and U.S. Pat. No. 5,006,394 (Baird). As well, suitable hydroformed films are disclosed in the following U.S. Patents, which are hereby incorporated herein by reference: U.S. Pat. No. 4,695,422 (Curro); U.S. Pat. No. 4,778,644 (Curro); and U.S. Pat. No. 4,839,216 (Curro).

FIG. 5 is a perspective illustration of a portion of the second layer 2000 comprising an apertured, macroscopically expanded, three dimension, fiber like, fluid pervious, polymeric web 2040, which is generally in accordance with the teachings of commonly assigned U.S. Pat. No. 4,342,314 (Radel).

The term "macroscopically expanded", as used herein, refers to webs, ribbons, and films which have been caused to conform to the surface of a three-dimensional forming structure so that both surfaces thereof exhibit a three-dimensional forming pattern of surface aberrations corresponding to the macroscopic cross-section of the forming structure, wherein the surface aberrations comprising the pattern are individually discernible to the normal naked eye (i.e. normal naked eye having 20/20 vision) when the perpendicular distance between the viewer's eye and the plane of the web is about 12 inches.

The term "fiber like" as used with reference to the appearance of plastic webs refers generally to any fine scale pattern of apertures, random or nonrandoin, reticulated or non-reticulated, which connote an overall appearance and impression of a woven or nonwoven fibrous web when viewed by the human eye.

As shown in FIG. 5, the web 2040 has a fiber-like appearance comprised of a continuum of fiber-like elements. The opposed ends of each of the fiber-like elements are interconnected to at least one other of the fiber-like elements. In the embodiment shown in FIG. 5, the interconnected fiber like elements form a pattern network of pentagonally shaped capillaries 2041. The web 2040 has a three-dimensional microstructure extending from the web's first surface 2042, in plane 2043, to the web's second surface 2044 in plane 2045. The term "microstructure" refers to a structure of such fine scale that its precise detail is perceived by the human eye only upon magnification.

The capillaries 2041 promote preferential flow from the first surface 2042 toward the second surface 2044. By "preferential flow" it is meant that, for a given pressure difference, a fluid flows more readily through the capillaries 2041 from the surface 2042 toward the surface 2044, than in the opposite direction from the second surface 2044 toward the first surface 2042.

Apertures 2047 in the surface 2042 are formed by a intersecting fiber-like elements, e.g., elements 2048, 2049, 2050, 2051, 2052. Each fiber-like element comprises a base portion 2054 located in plane 2043. Each base portion has a sidewall portion, e.g., sidewall portions 2056, attached to each edge thereof The sidewall portions 2056 extend generally in the direction of the second surface 2044 of the web 2040. The intersecting sidewall portions of the fiber-like elements are interconnected to one another intermediate the first and second surfaces of the web, and terminate substantially concurrently with one another in the plane 2045 of the second surface.

In FIG. 5, the interconnected sidewall portions 2056 terminate substantially concurrently with one another in the plane of the second surface 2045 to form apertures 2058 in the second surface 2045 of the web. The base portion 2054 can include a microscopic pattern of surface aberrations 2060 in accordance with U.S. Pat. No. 4,463,045, which aberrations provide a non-glossy surface and some degree of texture to the surface 2042. Even with the surface aberrations 2060, the first surface 2042 is relatively less textured than the second surface 2044.

Figure 4A:
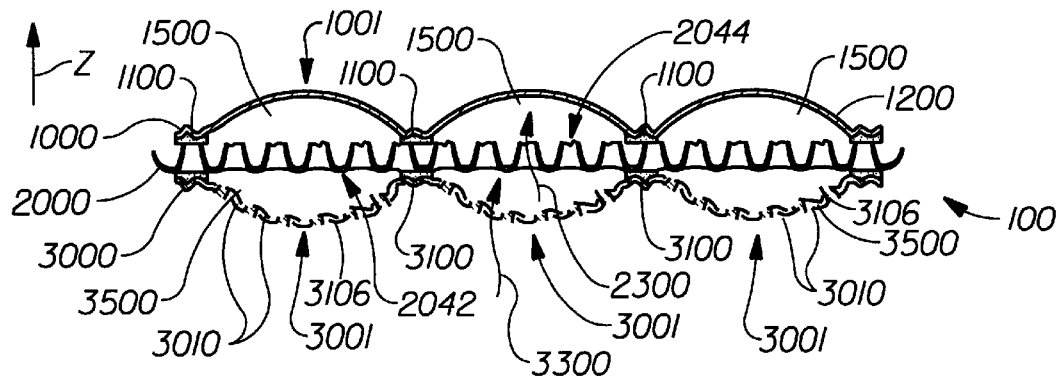
FIG. 4A is a cross-sectional illustration of a three layer embodiment of the present invention along Section 4—4 of FIG. 2, FIG. 4A showing a first layer, an apertured formed film second layer, and an apertured third layer after wetting, and wherein the second layer is joined to the first layer to provide preferential flow through apertures in the second layer toward the first layer.
Figure 4B:
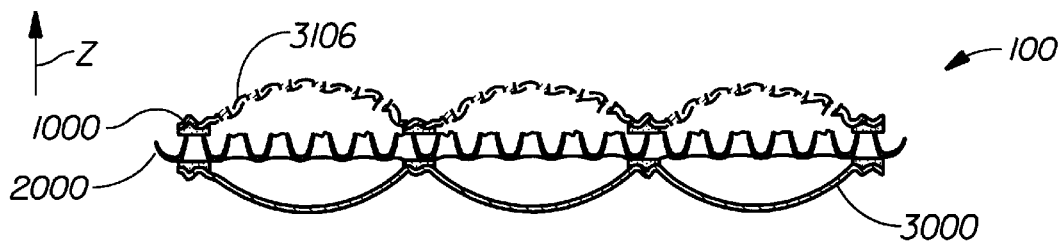
FIG. 4B is a cross-sectional illustration of a three layer embodiment of the present invention along Section 4—4 of FIG. 2, FIG. 4A showing a first layer, an apertured formed film second layer, and an apertured third layer after wetting, and wherein the second layer is joined to the apertured third layer to provide preferenitial flow through apertures in the second layer toward the third layer.

THIRD LAYER (THREE-LAYER EMBODIMENT):

The wipe 100 of the present invention may comprise three layers, as shown in FIGS. 2 and 4A–B. As shown, wiping article 100 comprises a first layer 1000, as described above, a second layer 2000 as described above, and a third layer 3000, described below. Third layer 3000 is preferably an apertured layer as shown, but may be unapertured. Apertures are preferably in the form of perforations or openings formed during the web formation of layer 3000. The apertures extending through the layer 3000 are designated by reference number 3010.

The third layer 3000 can comprise a woven or nonwoven web, as described above with respect to the first layer 1000. Apertures 3010 can be formed in any convenient manner, such as by mechanical means or by hydroforming. In one: embodiment, the third layer 3000 comprises an apertured paper web having a basis weight of about 32 gsm and a caliper of about 9 mils (0.009 inch) and the aperture can be formed using the forming belt shown and described in FIG. 5 of U.S. Pat. No. 5,245,025 issued Sep. 14, 1993, which patent is incorporated herein bf reference.

In one preferred embodiment, the third layer 3000 comprises a wetlaid paper web of cellulosic wood pulp fibers which is foreshortened at least about 4 percent, more preferably at least about 10 percent, and still more preferably at least about 20 percent, when wetted. Referring to FIG. 2, an apertured third layer 3000 is shown comprising crepe ridges 3015 corresponding to the foreshortening of the third layer 3000, such as by dry creping. The machine direction (MD) and cross machine direction (CD) are indicated in FIG. 2. The machine direction corresponds to the direction of manufacture of the web of third layer 3000. The crepe ridges 3015 are generally perpendicular to the machine direction, and generally parallel to the cross machine direction of the web of third layer 3000.

The web of the third layer 3000 can be a paper web having a basis weight of between about 15 to about 65 grams per square meter. In a preferred embodiment, the basis weight of the third layer 3000 is between about 25 to about 45 grams per square meter, and in a more preferred embodiment, the basis weight is between about 32 to about 35 grams per square meter.

In a more preferred embodiment, third layer 3000 comprises an apertured wetlaid paper web of cellulosic wood pulp fibers. Apertures 3010 can be formed in the third layer 3000 in any suitable manner. For instance, the apertures 3010 can be formed in the third layer 3000 during formation of the paper web of the third layer 3000, or alternatively, after the paper web of the third layer 3000 is manufactured. In one embodiment, the paper web of the third layer 3000 is produced according to the teachings of one or more of the following U.S. Patents, which Patents are incorporated herein by reference: U.S. Pat. No. 5,245,025 issued Sept. 14, 1993 to Trokhan et al.; U.S. Pat. No. 5,277,761 issued Jan. 11, 1994 to Phan et al.; and U.S. Pat. No. 5,654,076 issued Aug. 5, 1997 to Trokhan et al. In particular, U.S. Pat. No. 5,277,761 at Column 10 discloses formation of a paper web having a apertures.

Prior to wetting of the first layer, the creped third layer 3000 can have between about 4 and about 300 apertures 3010 per square inch, and more preferably between about 4 and about 100 apertures 3010 per square inch. Wetting a creped paper web causes the web, if unrestrained, to expand in at least one direction, such as the machine direction, so that the number of apertures 3010 per square inch after wetting can be smaller than the number of apertures per square inch prior to wetting. Similarly, when apertures are formed in a paper web, and the paper web is subsequently creped, the number of apertures per square inch prior to creping will be smaller than the number of apertures per square inch after creping. Accordingly references to paper web dimensions refer to dimensions after creping and prior to wetting.

The apertures 3010 can comprise between about 15 and about 75 percent of the total surface of the third layer 3000. The apertures 3010 shown in FIG. 2 are bilaterally staggered (staggered in both the machine and cross machine directions) in a repeating, nonrandom pattern. In one embodiment, the third layer 3000 comprises a paper web which is dry creped 30 percent (30 percent foreshortening) with greater than about 25 percent wet extensibility, and has about 40 to about 50 apertures 3010 per square inch, the apertures 3010 having a length of about 0.10 to about 0.18 inch and a width of about 0.07 to about 0.15 inch, and a distance between apertures 106 of about 0.05 to about 0.08 inch.

The paper web is manufactured by first forming an aqueous papermaking furnish. The furnish comprises papermaking fibers, and can further comprise various additives. U.S. Pat. No. 5,223,096 issued Jun. 29, 1993 to Phan et al. is incorporated herein by reference for the purpose of disclosing various wood pulps and papermaking additives.

A suitable paper web for making the third layer 3000 can be manufactured according to the following description. A papermaking furnish is prepared from water and highly refined Kraft pulp derived from northern softwoods (NSK), the paper furnish having a fiber consistency of about 0.2 percent (dry fiber weight divided by the total weight of the furnish equals 0.002). A dry strength additive such as carboxymethyl cellulose (CMC) is added to the 100% NSK furnish in the amount of about 5 pounds of CMC solids per ton of dry papermaking fibers. A wet strength additive such as Kymene 557H (available from Hercules, Inc. of Wilmington, Del.) is added to the furnish in the amount of about 28 pounds of Kymene solids per ton of dry papermaking fibers. The apertured third layer 3000 preferably has a wet extensibility greater than that of the second layer 2000. The apertured layer 3000 preferably has a wet extensibility of at least about 4 percent, more preferably at least about 10 percent, most preferably at least about 25 percent. The wet extensibility of the apertured layer 3000 can be provided by foreshortening the web, such as by dry creping the web.

Selected portions of the third layer 3000 are joined, directly or indirectly, to second layer 2000 to inhibit wet extension of the third layer in the plane of the third layer, in a similar fashion and pattern as first layer 1000 is bonded to second layer 2000. Selected portions of the third layer 3000 are joined directly to the second layer 2000 at bond areas designated 3100. Bonding methods and patterns are generally in accordance with the methods and patterns disclosed above with reference to first layer 1000. While the Figures show bond patterns between the first layer and second layer in registry with the bond patterns between the third and second layer, registry is not necessary. As a practical matter, to reduce complexity in processing a three-layer embodiment of the present invention, having bond patterns in registry may be preferred.

When the first and third layers are wetted, the first layer 1000 deforms to provide dome-like protuberances 1001 and pockets 1500, and the third layer 3000 deforms to provide dome like protuberances 3001 and pockets 3500. Therefore, just as for the two layer embodiment described above, one beneficial property of a three layer wipe of the present invention is that the wet caliper is greater than the dry caliper. In particular, the three-layer wipe 100 has a wet caliper to dry caliper ratio which is greater than 1.0, and preferably at least about 1.1, more preferably at least about 1.5, and even more preferably greater than about 2.0. The wet caliper to dry caliper ratio is a measure of the thickness of the wipe 100, when wetted, relative to the thickness of the dry wipe 100 prior to wetting. The wet caliper to dry caliper ratio is measured according to the procedure "Wet Caliper to Dry Caliper Ratio" provided below.

Another advantage is recognized when third layer 3000 is apertured. As shown in FIGS. 4A and 4B, in addition to the formation of dome-like protuberances 3001, the wet extension of third layer 3000 around apertures 3010 forms what can best be described as cusps 3106, or surface irregularities formed by the deformation apertures 3010 upon wet extension. Cusps 3106 provide added texture to the surface of wipe 100 which can be modified as needed by adjusting the size and spacing of apertures 3010.

In one embodiment, the apertures 3010 of the third layer 3000 are larger than the apertures of the second layer 2000.

Prior to wetting of the first layer, the creped third layer 3000 can have between about 4 and about 300 apertures 3010 per square inch, and more preferably between about 4 and about 100 apertures 3010 per square inch. Wetting a creped paper web causes the web, if unrestrained, to expand in at least one direction, such as the machine direction, so that the number of apertures 3010 per square inch after wetting can be smaller than the number of apertures per square inch prior to wetting. Similarly, when apertures are formed in a paper web, and the paper web is subsequently creped, the number of apertures per square inch prior to creping will be smaller than the number of apertures per square inch after creping. Accordingly references to paper web dimensions refer to dimensions after creping and prior to wetting.

The apertures 3010 can comprise between about 15 and about 75 percent of the total surface of the third layer 3000. The apertures 3010 shown in FIG. 2 are bilaterally staggered (staggered in both the machine and cross machine directions) in a repeating, nonrandom pattern. In one embodiment, the third layer 3000 comprises a paper web which is dry creped 30 percent (30 percent foreshortening) with greater than about 25 percent wet extensibility, and has about 40 to about 50 apertures 3010 per square inch, the apertures 3010 being generally elongated, e.g., in a modified oval shape, having a longest dimension (i.e., length) of about 0.10 to about 0.18 inch and a shortest dimension (i.e., width) of about 0.07 to about 0.15 inch, and a distance between apertures of about 0.05 to about 0.08 inch.

As shown in FIG. 4A, a three layer arrangement provides a two stage filter for liquids and small solid particles. The third layer 3000, bonded to the less textured side 2042 of second layer 2000, provides the first filter stage, and the second layer 2000 provides the second filter stage. Liquid carrying small solid particles can pass through the relatively large apertures 3010 along flow path 3300, to be trapped in pockets 3500. Fluid and small particles can subsequently pass through the second layer 2000 along flow path 2300, to be trapped in pockets 1500. The second layer 2000 and the first layer 1000 can contain the solids particles that are trapped in pockets 1500.

Alternatively, third layer 3000 may be bonded to the more textured side 2044 of second layer 2000 as shown in FIG. 4B. Such a structure maximizes the texture on one side of wipe 100, thereby providing increased sudsing and lathering of cleaning agents in or on the web 100.

BONDING:

Preferably, selected portions of the first layer 1000 and (if used) the third layer 3000 are joined to the second layer 2000 in a predetermined bonding pattern. The bonding pattern will be described with reference to the first layer 1000, with the understanding that the description can also apply to the third layer 3000. Alternatively, the third layer 3000 could be joined to the second layer 2000 with a different bonding pattern, or by a different mechanism (e.g. using adhesives, ultrasonic bonding for example).

The first layer 100 and the second layer 200 can be joined using any suitable method, including but not limited to adhesive bonding, mechanical bonding, thermal bonding, mechanical-thermal bonding, ultrasonic bonding, and combinations thereof In particular, adhesive 300 FIGS. 1 and 2) can be applied by printing methods, such as gravure printing, reverse gravure printing, screen printing, flexographic printing, and the like. In one embodiment, EVA hot melt adhesive may be screen printed in a lattice pattern generally as shown in FIGS. 1 and 2. A suitable screen printer is a ITW Dynatec Model SP-117. A suitable screen for this printer is a 40 mesh Galvano screen manufactured by Rothtec Engraving Corp., New Bedford, Mass.

The adhesive is preferably water insoluble so that the wipe 100 can be wetted with water without delamination of the layers. The adhesive is preferably also surfactant tolerant. By "surfactant tolerant" it is meant that the bonding characteristics of the adhesive are not degraded by the presence of surfactants. Suitable adhesives include EVA (ethylene vinyl acetate) based hot melt adhesives. One suitable adhesive is a hot melt adhesive commercially available as H1382-01 from Ato-Findley Adhesives of Wauwatos, Wis.

Figure 6:
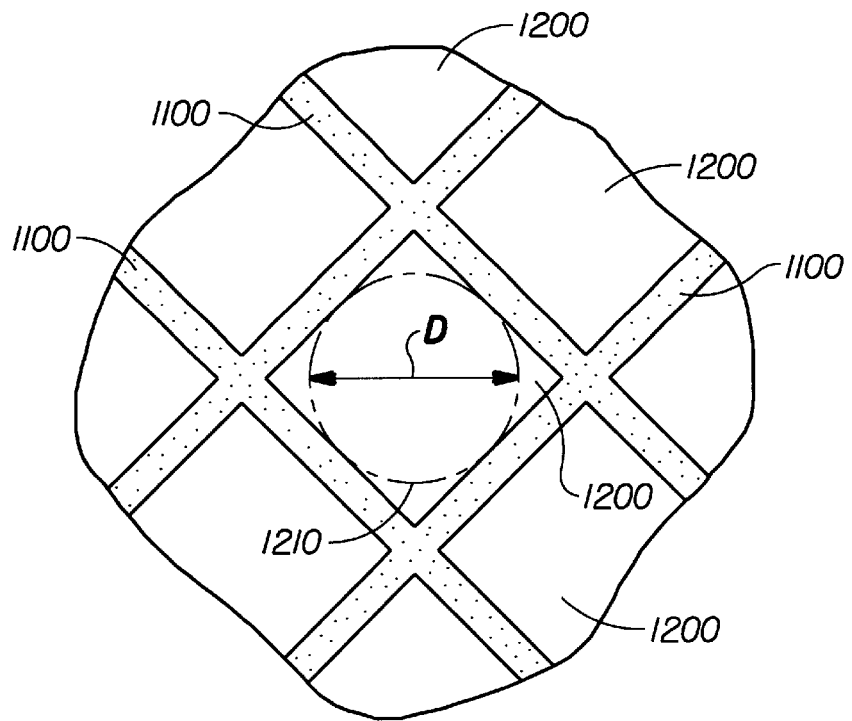
FIG. 6 is a schematic plan view illustration of a portion of a disposable wilping article of the present invention showing an unbonded portion of the first layer including a circular portion inscribed within a continuous bonding pattern.

Referring to FIGS. 1 and 6, the bond areas 1100 of the first layer 1000 preferably form a continuous network bonding pattern. The continuous network pattern defines discrete, unconnected unbonded regions 1200. In FIGS. 1 and 6, the unbonded regions 1200 are in the shape of diamonds, but it will be understood that the regions 1200 could also have other shapes, including but not Unite to circles, squares, ovals, triangles, as well as other regular and irregular polygons, and the like.

Figure 7:
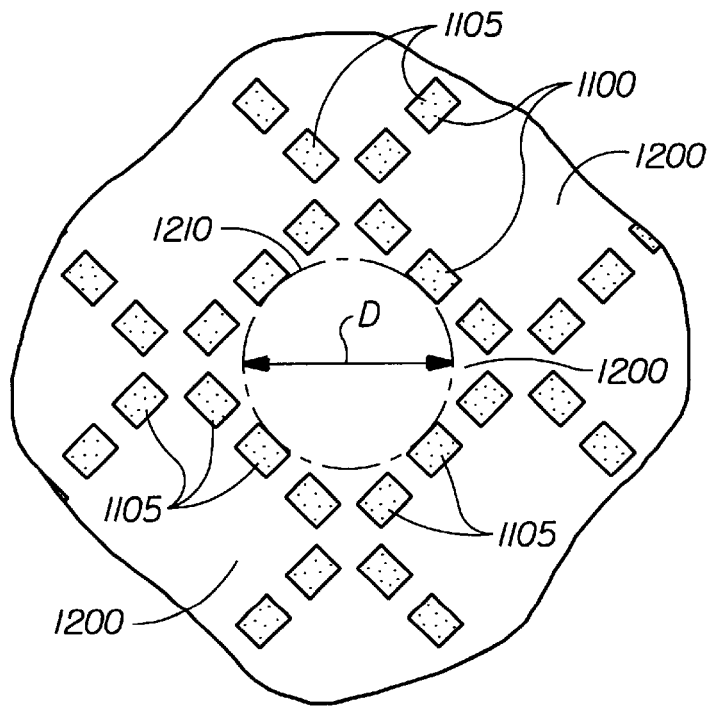
FIG. 7 is a schematic illustration similar to that of FIG. 6 showing an unbonded portion of the first layer including a circular portion inscribed within a discontinuous bonding pattern.

Alternatively, while a continuous network is currently preferred, it is contemplated that discontinuous, or essentially continuous, bond patterns, such as shown in FIG. 7, may also provide for the desired caliper increase according to present invention. As shown, a discontinuous pattern of closely spaced bond sites can approach a continuous pattern, depending on the spacing between adjacent bond sites. Without being bound by theory, it is believed that such adjacent bond sites should be less than about one inch from one another, more preferably 0.5 inch, and more preferably less than 0.1 inch. Without wishing to be bound by theory, in principle, the more a particular bond pattern approaches a continuous network, the more pronounced are the benefits of the present invention. In FIG. 7, the bond areas 1100 comprise discrete bond sites 1105. The discrete bond sites 1105 outline interconnected unbonded regions 1200. The discrete bond sites taken as a whole form an essentially continuous network.

The unbonded regions 1200 of the first layer 1000 can each include a circular area inscribed within the bonding pattern. The circular area is indicated by reference number 1210 in FIGS. 6 and 7. The diameter D of the inscribed circular area 1210 should be at least 0.1 inch in order to generate a sufficient increase in caliper and bulk of the article 100 when wetted. Preferably, the diameter D is at least 0.2 inch, anid most preferably at least 0.4 inch. The diameter D is preferably less than 3.0 inches to provide visually distinct protuberances 1001, and to provide protuberances 1001 without excessive wrinling. In one embodiment the diameter D is less than 2.0 inch.

The first, second, and third layers can be joined together by positioning the second layer between the first and third layers, and then passing the three layers together through a heated embossing nip. The embossing nip can include a smooth anvil roll and a patterned embossing roll corresponding to the desired bonding pattern.

EXAMPLE OF A PREFERRED EMBODIMENT

This example illustrates the preparation of a three-layer disinfecting/cleaning wipe comprising a differentially extensible multi-layer absorbent article, suitable for use with disinfecting/cleaning lotion. This article is manufactured by selectively bonding a paper substrate to both sides of a polymeric web.

A. First Layer Preparation

The paper web was a 100% NSK, non-layered sheet with a basis weight of 20 lbs/ream (about 32.5 gsm). The paper had a plurality of high basis weight zones and low basis weight zones, produced generally according to the teachings of aforementioned U.S. Pat. No. 5,503,715 (Trokhan, et al) with the following specifics:

1) The forming wire contained 100 protuberances per square inch.
2) The protuberances occupied about 50% of the surface area of the formiing wire.
3) The protuberances extended above the forming wire reinforcing structure about 0.008 inches.
4) The apertures of each protuberance occupied about 10% of the surface area of the forming wire.
5) In the wet end of the conventional papermaking process carboxy-methyl-cellulose (CMC) was injected into the NSK pulp slurry at a ratio of 6 pounds of CMC solids per ton of dry paper.
6) In the wet end of the conventional papermaking process of Kymene 557H (Available from Hercules Inc.) was injected into the NSK pulp slurry at a ratio of 20 pounds of Kymene solids per ton of dry paper.
7) The paper was creped at 25%, i.e., the foreshortened length after reaching the creping blade is 25% less than the length of the web before the creping blade.

B. Third (Apertured) Layer Preparation:

The apertured paper web was a 100% NSK, non-layered sheet with a basis weight of about 20 lbs/ream (about 32.5 gsm). The paper had a plurality of high basis weight zones as well as a plurality of apertures of essentially zero basis weight. The paper was produced according to the teachings of the aforementioned U.S. Pat. No. 5,503,715 (Trokhan, et al) with the following specifics:

1) The forming wire contained 37 protuberances per square inch.
2) The protuberances occupied about 36% of the surface area of the forming wire.
3) The protuberances extended above the forming wire reinforcing structure about 0.025 inches.
4) In the wet end of the conventional papermaking process carboxy-methyl-cellulose (CMC) was injected into the NSK pulp slurry at a ratio of 6 pounds of CMC solids per ton of dry paper.
5) In the wet end of the conventional papermaking process of Kymene 557H (Available from Hercules Inc.) was injected into the NSK pulp slurry at a ratio of 20 pounds of Kymene solids per ton of dry paper.
7) The paper was creped at 25%, i.e., the forshortened length after reaching tie creping blade is 25% less than the length of the web before the creping blade.

C. Second Layer Preparation:

The restraining web was a three-dimensional, macroscopically-expanded web of polymeric materials prepared generally in accordance with the teachings of the aforementioned U.S. Pat. No. 4,342,314 (Radel). The film was manufactured with the following specifications:

1). The composition was 100% low density polyethylene.
2). The overall caliper was between 19 and 20 mils.
3). The apertures made up about 20% of the total area.
4). The basis weight was about 15.4 lb/3000 sqft (25 gsm).

D. Bonding:

To prepare a composite sample, a heated press capable of pressing up to 5000 psi was used. The top platen was heated to 160° F. and the bottom platen was heated to 215° F. Also, a patterned die was used to create the bonding pattern and was supported by the bottom platen of the press. This bonding pattern consisted of parallel raised lines in one direction, intersecting parallel raised lines in a second direction, generally as shown in FIG. 1. The pattern was formed on dies 12×12 inch square, 3/16 inch thick, with the raised areas 3/16 inch high, 0.1 inch wide, spaced 0.5 inch apart.

A packet was assembled which consisted (from the bottom up) of the variable basis weight web, constraining web, apertured paper web, as described above, as well as second variable basis weight web. [Note: the second variable basis weight wet functions as a cover sheet to prevent the polymer inner layer from adhering to the upper platen of the press through the apertures in the paper layer. It is, therefore, not part of the finished wipe.]

The packet was placed in the press on top of the patterned die. The press was engaged for 7–9 seconds at a pressure of about 5000 psi. The sample was then rotated 80 degrees and the press re-engaged for an additional 7–9 seconds. This method produces a diamond embossed pattern which is aesthetically appealing in appearance.

After the laminate structure has been embossed, the variable basis weight web nearest the apertured paper web (i.e., the cover sheet) is removed. The product is cut to the appropriate dimensions, 8.5" by 11", and the edges are sealed with an iron (e.g. Harwil Corp.model T-7).

WET EXTENSIBILITY TEST

The wet extensibility of a layer, such as the layer 100 or the layer 200, is determined using the following procedure. Samples are conditioned at 70 degrees Fahrenheit and 50 percent relative humidity for two hours prior to testing.

First, the direction of greatest wet extensibility in the plane of the layer is determined. For dry creped paper webs, this direction will be parallel to the machine. direction, and generally perpendicular to the crepe ridges.

If the direction of greatest wet extensibility is not known, the direction can be determined by cutting seven samples from a sheet with sample lengths oriented between 0 degrees and 90 degrees, inclusive, with respect to a reference line drawn on the sheet. The samples are then measured as set forth below to determine the direction of greatest wet extensibility.

Once the direction of the greatest wet extensibility is determined, 8 samples are cut to have a length of about 7 inches measured parallel to the direction of greatest wet extensibility, and a width of at least 1 inch. The samples are cut from unbonded portions of the layers 100 and 200, or, if unbonded portions having the above dimensions cannot be cut from the article 20, then samples are cut from the layers 100 and 200 prior to bonding the layers together. Two marks are placed on each sample, such as with an ink pen. The marks are spaced apart 5 inches as measured parallel to the direction of greatest wet extensibility. This 5 inch length is the initial dry test length of the sample.

Each sample is thoroughly wetted by submerging the sample in distilled water for 30 seconds in a water bath. Each sample is removed from the water bath and immediately supported to hang vertically so that a line through the two marks is generally vertical. The wet sample is supported such that the support does not interfere with extension between the two marks (e.g. with a clip which does not contact the sample between the two marks). The wet test length of the sample is the distance between the two marks. The distance is measured within 30 seconds of removing the sample from the water bath.

For each sample, the percent wet extension is calculated as

Percent Wet Extension=(wet test length−initial dry test length)/(initial dry test length)×100

For example, for a measured wet test length of 6.5 inches and an intial dry test ngth of 5.0 inches, the wet extension is ((6.5−5)/5)×100=30 percent.

The wet extensibility of the samples is the average of 8 calculated values of sample wet extension.

WET CALIPER TO DRY CALIPER RATIO:

The wet caliper to dry caliper ratio is measured using a Thwing-Albert Instrument Co. Electronic Thickness Tester Model II, using the following procedure. Samples are conditioned at 70 degrees Fahrenheit and 50 percent relative humidity for two hours prior to testing.

The dry caliper of the article 20 is measured using a confining pressure of 95 grams per square inch and a load foot having a diameter of 2 inches. The dry caliper is measured for eight samples. For each sample, the caliper is measured with the load foot centered on an unbonded region of the first layer 100. The eight caliper measurements are averaged to provide an average dry caliper.

Each sample is then wetted by submerging the sample in a distilled water bath for 30 seconds. The sample is then removed from the water bath. The caliper of the wet sample is measured within 30 seconds of removing the sample from the bath. The wet caliper is measured in the same location in which the dry caliper was previously measured. The eight wet caliper measurements are averaged to provide an average wet caliper. The wet caliper to dry caliper ratio is the average wet caliper divided by the average dry caliper.

What is claimed is:

1. A multiple layer disposable wiping article comprising:
    a first layer comprising a nonwoven web, the first layer being extensible in a plane of the first layer when the first layer is wetted; and
    a second layer comprising a plastic film, the plastic film being less extensible when wetted than the first layer;
    wherein selected portions of the first layer are joined to the second layer to inhibit wet extension of the first layer in the plane of the first layer, and wherein the article has a wet to dry caliper ratio of at least about 1.1.

2. The article of claim 1, wherein the first layer comprises a wetting agent prior to use of the article, and wherein the wetting agent induces deformations of the first layer in a direction normal to the plane of the first layer.

3. The article of claim 1, wherein selected portions of the first layer are joined to the second layer in a predetermined bonding pattern to provide a plurality of unbonded regions of the first layer.

4. The article of claim 1, wherein the first layer has a wet extensibility of at least about 4 percent.

5. The article of claim 1, wherein the first layer has a wet extensibility of at least about 10 percent.

6. The article of claim 1, wherein the first layer has a wet extensibility of at least about 20 percent.

7. The article of claim 1, wherein the first layer has a wet extensibility of at least about 25 percent.

8. The article of claim 1, wherein the nonwoven web is a creped cellulosic web, and wherein the plastic film is a macroscopically expanded three dimensional film having apertures.

9. The article of claim 8, wherein the plastic film has a caliper of at least about 5 mils.

10. The article of claim 8, wherein the plastic film exhibits a preferred fluid flow direction through the apertures, and wherein the plastic film is oriented relative to the first layer such that the preferred flow direction through the apertures is toward the first layer.

11. The article of claim 8, wherein the plastic film exhibits a preferred fluid flow direction through the apertures, and wherein the plastic film is oriented relative, to the first layer such that the preferred flow direction through the apertures is away from the first layer.

12. The article of claim 1, wherein the plastic film comprises a first surface and a second surface, and wherein the second surface is relatively more textured than the first surface.

13. The article of claim 1, wherein the article comprises a pre-moistened wipe;
    wherein the first layer comprises a creped web, the web comprising cellulosic fibers;
    wherein the second layer comprises an apertured three dimensional plastic film;
    wherein selected portions of the first layer are bonded to the second layer in a predetermined bonding pattern to provide a plurality of unbonded regions of the first layer; and
    wherein the first layer comprises a wetting agent prior to use of the article, wherein the wetting agent provides deformation of the first layer in a direction normal to the plane of the first layer.

14. The article of claim 1, wherein the wet to dry caliper ratio is at least about 1.2.

15. The article of claim 1, wherein the wet to dry caliper ratio is at least about 1.4.

16. A multiple layer disposable wiping article comprising:
    a first layer, the first layer being extensible in a plane of the first layer when the first layer is wetted;
    a second layer comprising a three dimensional apertured plastic film the plastic film being less extensible when wetted than the first layer; and
    an apertured third layer, the third layer being extensible in a plane of the third layer when the third layer is wetted;
    wherein the second layer is disposed intermediate the first layer and the third layer and wherein the selected portions of the first layer and the third layer are joined to the second layer to inhibit wet extension of the first layer and the third layer in the planes of the first layer and the third layer, respectively, and wherein the article has a wet to dry caliper ratio of at least about 1:1.

17. The article of claim 16, wherein the wet to dry caliper ratio is at least about 1.4.

18. The article of claim 16, wherein the wet to dry caliper ratio is at least about 2.0.

* * * * *